United States Patent [19]
Heubeck et al.

[11] Patent Number: 4,813,060
[45] Date of Patent: Mar. 14, 1989

[54] DENTAL X-RAY DIAGNOSTIC APPARATUS FOR PRODUCING PANORAMA TOMOGRAMS OF THE JAW OF A PATIENT

[75] Inventors: Erich Heubeck; Werner Günther; Manfred Müther, all of Bensheim; Leonhard Werner, Erlangen, all of Fed. Rep. of Germany

[73] Assignee: Siemens Aktiengesellschaft, Berlin and Munich, Fed. Rep. of Germany

[21] Appl. No.: 942,812

[22] Filed: Dec. 17, 1986

[30] Foreign Application Priority Data

Dec. 20, 1985 [DE] Fed. Rep. of Germany ....... 3545493

[51] Int. Cl.$^4$ .............................................. G03B 41/16
[52] U.S. Cl. ......................................... 378/39; 378/38
[58] Field of Search ......................... 378/38, 39, 40, 97

[56] References Cited

U.S. PATENT DOCUMENTS

| | | |
|---|---|---|
| 2,434,827 | 1/1948 | Akers . |
| 3,908,126 | 9/1975 | Hudson et al. . |
| 4,021,672 | 5/1977 | Franke . |
| 4,039,837 | 8/1977 | Ohta et al. . |
| 4,158,138 | 6/1979 | Hellstrom . |
| 4,194,121 | 3/1980 | Cushman . |
| 4,418,419 | 11/1983 | Schreiber et al. . |
| 4,475,224 | 10/1984 | Grassme ................................ 378/38 |
| 4,495,632 | 1/1985 | Nakano ................................. 378/38 |
| 4,495,632 | 1/1985 | Nakano . |

FOREIGN PATENT DOCUMENTS

3503465  8/1985  Fed. Rep. of Germany .

Primary Examiner—Carolyn E. Fields
Assistant Examiner—Joseph A. Hynds

[57] ABSTRACT

A dental diagnostic apparatus or installation which obtains a better matching of the exposure data to the patient and has a rotary unit carrying the radiation source and the film cassette which are adjustable to an initial position by an adjustment arrangement and from this initial position the film cassette can be charged with the radiation within the framework of normal transillumination with the radiation initially beginning outside of the mandibular arch. The incoming radiation dose is measured by a detector arrangement which creates a signal that is compared in a computational unit of a control arrangement to a rated quantity corresponding to a prescribed dose value. The exposure data required from further transillumination of the patient's head are identified therefrom and the tomogram position is determined by identifying the patient-associated film speed via the jaw length/jaw width measurements and comparison to defined rated value.

12 Claims, 4 Drawing Sheets

DENTAL X-RAY DIAGNOSTIC APPARATUS FOR PRODUCING PANORAMA TOMOGRAMS OF THE JAW OF A PATIENT

BACKGROUND OF THE INVENTION

The invention relates to a dental x-ray diagnostic installation for producing panoramic tomograms of the jaw of a patient. The apparatus or installation includes a rotary unit which contains a carrier for supporting a radiation source and also supporting a film cassette holder for accepting film cassettes, an arrangement by which the carrier is adjustably rotated around a vertical axis and the axis is moved along an orbital curve corresponding to the dental arch of the patient. Another feature is that the film cassette holder or the film cassette insertable therein is adjustable, both so that teeth are successively imaged on the film together with the jaw and includes at least one detector arrangement adjacent to the film cassette which arrangement supplies electrical signals corresponding to a dose rate of radiation impinging thereon and provides a signal to a control for at least the tube voltage of the radiation source.

U.S. Pat. No. 4,021,672, which is based on German application No. 24 47 075 and whose disclosures are incorporated by reference, is an example of a known x-ray diagnostic installation or apparatus. In this known device, the head of the patient is held in a corresponding retension means. During the exposure, the x-ray source and film cassette holder move around the head of the patient. The carrier and the film cassette holder are thereby rotated around a vertical axis so that the x-rays always impinge on the jaw, or respectively the teeth, to be exposed at essentially a right angle so that the distance between the teeth and film remains essentially constant. As a consequence of the relative motion between the film cassette and the radiation source, the teeth are successively imaged on the film together with the jaw.

In accordance with the previous techniques, the exposure data or settings (kV, mA, sec) with which the radiation source is operated are visually and emperically determined by the user. For example, user will emperically identify in accordance with value pairs for the kV/mA prescribed by the manufacturer for various body sizes for a child, a youth, an adult, and extra large, and then the emperically identified value pairs are set into the apparatus.

It can be easily understood that such a selection of the exposure data undertaken in a purely visual way cannot always be optimum and assumes great experience on the part of the apparatus user or operator. Further, it is not possible, given the known apparatus, to produce a patient-related tomogram position or, respectively, this is possible only in an extremely complicated way.

SUMMARY OF THE INVENTION

The object of the present invention is is to achieve an improvement in a x-ray diagnostic installation or apparatus with which a simpler and better matching of the exposure data and tomogram position to the patient can be achieved so that an optimum film density can be achieved, and a lower x-ray exposure load for the patient is achieved. To accomplish these goals, the present invention is directed to an improvement in a dental x-ray diagnostic apparatus for producing panoramic tomograms of the jaw of a patient, said apparatus comprising a rotary unit which contains a carrier, a radiation source mounted on the carrier, a film cassette holder for accepting a film cassette being mounted on the carrier, and adjustment means with which the carrier is rotated around an first adjustable vertical axis and the axis is adjusted to move around an orbit curve corresponding to the dental arch so that the film cassette holder and the film cassette inserted therein are both adjusted so that the teeth are successively imaged on the film together with the jaw and further contain at least one detector arrangement adjacent to the cassette, said detector arrangement supplying an electrical signal corresponding to dose rates of an x-radiation incident thereon for the control of at least the tube voltage kV of the radiation source. The improvements are that the rotary unit is adjusted into an initial position by control means for operating the adjustment means, said control means actuating the generator of the radiation source to direct rays from the source outside of one end of the mandibular arch and onto the film cassette, this incoming radiation dosage being measured by means of the detector means and the signal corresponding to the radiation dosage being applied to a computation unit or means in which a quantity corresponding to the signals is compared to a quantity corresponding to the prescribed dosed value and the control means selecting exposure settings for mA, kV and time required for the transillumination of the appertaining patient as identified from this comparison and the generator for the radiation sources being controlled with the exposure data or settings. In accordance with the proposal of the invention, the incoming radiation dose is identified by means of a detector arrangement in the framework of the standard transillumination which first begins outside of the mandibular arch and this incoming radiation dosage is compared to a defined dose value which has been recorded in a memory. This rated dose value represents the personal degree of density which the physician determines on the basis of the film and development material employed for the selected film cassette format and may potentially be determined on the basis of yet further factors. This rated value is advantageously adjustable in accordance with desired degrees of density. For the comparison of the dose values, the provided computation identifies the exposure data or setting such as mA, kV and time required for the transillumination of the appertaining patient's head. The transillumination then occurs in accordance with the prescribed execution curve with the exposure data identified in this way.

The optimum tomographic layer position to be identified for the patient is advantageously identified in that the time from the beginning of the charging of the film cassette with rays initially proceeding outside of the mandibular arch is measured up to the time a skip function is reached, i.e., up to the beginning of the transillumination of the jaw and the jaws length (development of the jaw and the film) and the jaw's breadth (the jaw's width) are first identified from this time. To this end, the path which belongs to the elapsed time identified up to reaching the skip function is identified relative to the overall time required in order to expose the full jaw and to the overall path on the film appertaining thereto and the jaw length is then calculated for the overall path minus the sub-path preceding and following the transillumination of the jaw. With the assistance of an emperically identified conversion factor, the jaw width is then identified in turn from the jaw length. Either a comparison to prescribed, arbitrarily finely graduated rated values or rated values which are also individually calculated, the optimum film rate to be provided for the appertaining patient is in accordance with his personal jaw configuration can be identified for the jaw width. Finally, the optimum tomographic layer position can be identified with the individually identified film rate, which advantage cannot be achieved with prior known apparatus.

Other advantages and improvements will be readily apparent from the following drawings, description of the preferred embodiments and claims.

DESCRIPTION OF THE PREFERRED EMBODIMENTS

Figure 1:
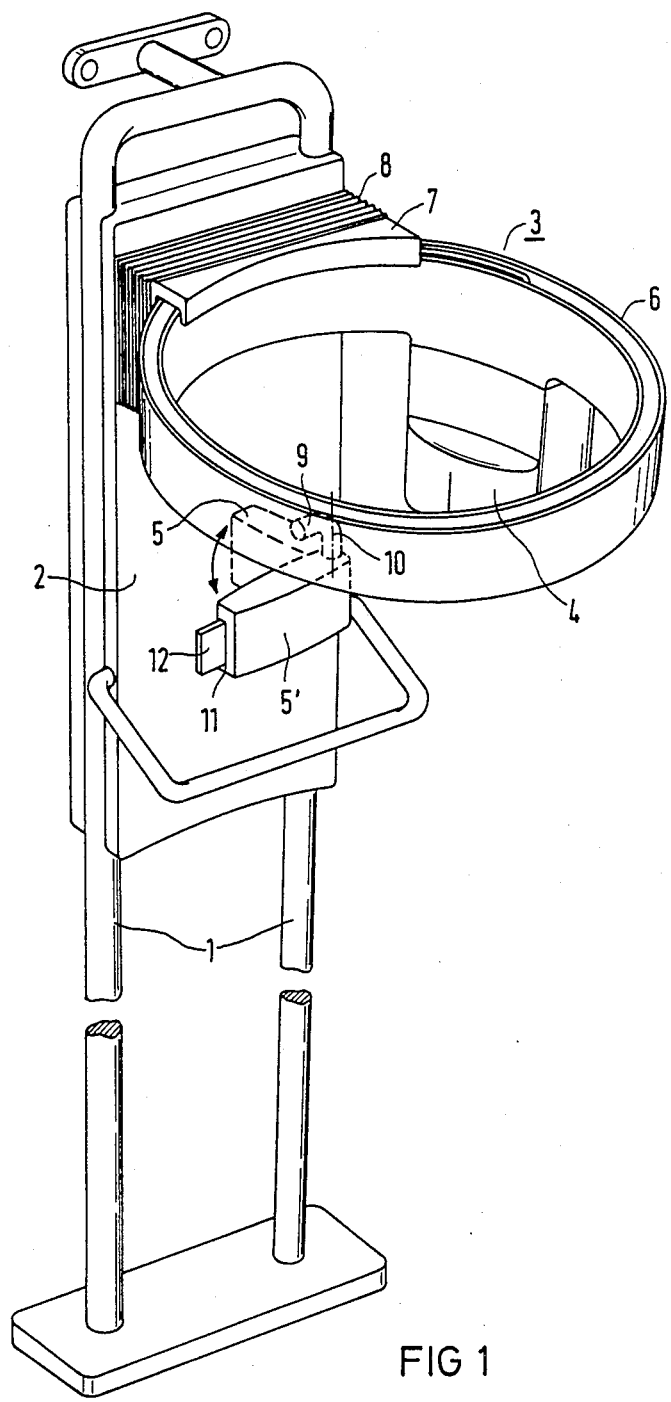
FIG. 1 is a perspective view in accordance with the present invention.

The principals present in the invention are particularly useful in the x-ray diagnostic installation or apparatus of FIG. 1. The apparatus contains a support 1 formed of two stand pipes, a truck or carriage 2, which is arranged in a height-adjustable fashion on the support 1. A rotary unit 3 is supported on the truck 2 and this unit includes a self-contained turntable type ring 6, which is mounted in a bearing part 7 for both rotation around a center axis and for pivoting or swivelling around a swivel axis. An x-ray source 4 is mounted on the ring 6 and also mounted on the ring 6 diametrically opposite to the source 4 is a film cassette holder 5. The adjustment means, which is necessary for both rotating the ring and also swivelling the ring around the swivel axis, is covered in FIG. 1 by an accordion bellows 8 which extends between the truck or carriage 2 and the turntable ring 6.

Figure 2:
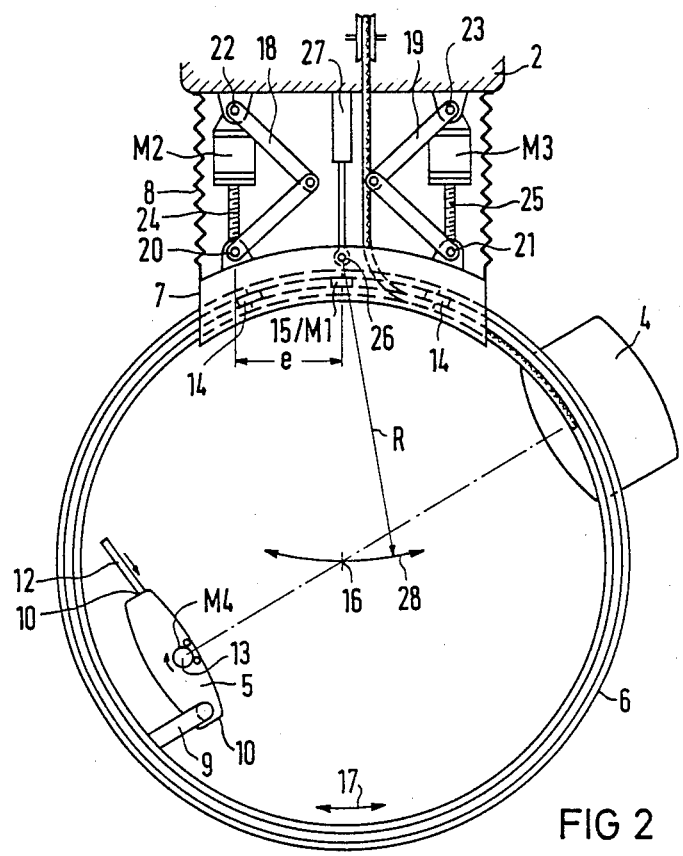
FIG. 2 is a plan view with portions removed for purpose of illustration of the adjustment mechanism for the apparatus of FIG. 1.

While the radiation source 4 is rigidly mounted on the turntable ring 6, the film cassette holder 5 is held at the free end of an angled carrier arm 9 which is secured to the turntable ring 6 and is held so it can pivot around a vertical axis 10. For better patient positioning or, respectively, for special exposures such as CEPH exposures, the film cassette holder 5 can be brought from the use position shown in broken lines in FIG. 1 into a non-use position 5' shown in solid lines. The film cassette holder 5 contains a slot 11 at each of its two end faces and the film cassette 12, which contains the film to be exposed, is introduced via the slot 11 and is withdrawn from the other after the film has been exposed. To move the film cassette 12 through the cassette holder 5, a transport means 13 which is composed of a drive motor M4 coupled to a drive capstan and two back pressure rollers which are arranged in a fashion corresponding to the capstan, are provided (see FIG. 2). This transport means will move the cassette 12 past an exposure location or secondary diaphragm at which the central rays from the source 4 will impinge and transport means will move this cassette 12 at the defined or desired speed of advance or transport.

The turntable ring 6 is rotatably held in the bearing part 7. To this end and upon formation of a triangular bearing support, two guide rollers 14 are provided and engage the lower annular edge surface of the ring in the bearing part 7 while a drive roll or capstan 15 is provided between the two rollers 14 and is arranged to engage the upper annular edge of the ring. The drive capstan 15 is coupled to a first drive motor M1 which is not shown in greater detail. By this friction drive, the turntable ring can be turned around a center axis 16 in either direction as indicated by the double-headed arrow 17.

In addition to the rotation of the ring 6 around the axis 16, adjustment of the turntable ring 6 relative to the truck 2 is still possible. To this end, two pairs of scissor arms 18 and 19 are provided with one end of the arm 18 being connected by a pivotal connection 20 to the bearing part 7 and the other end being connected by a pivotal connection 22 to the carriage 12. In a similar manner, the pair of scissor arms 19 have one end connected by a pivotal connection 21 to the bearing part 7 and the other end connected by a pivotal connection 23 to the carriage. Spindle drives 24 and 25 are provided between the points of articulation or the pivotal connections and have drive motors M2 for the spindle 24 and M3 for the spindle drive 25. These drive motors M2 and M3 are capable of being individually driven as shall yet be set forth so that the turntable ring can be adjusted to be moved parallel or obliquely relative to the truck 2 in addition to its rotation around the axis 16. To this end, the bearing part 7 is pivotally connected by a pivot bearing 26 to an end of a telescopic arm 27 which is rigidly mounted on the carriage or truck 2 in a central position between the two connections 20 and 21 at a distance e. In conjunction with the forementioned scissor arm structure, it is thus possible to swivel the turntable ring around the axis 26 by only actuating one of the two motors M2 and M3, or actuating them at a different rate or direction. This swivelling will move the axis of rotation for the ring 6 on a curve 28 for a distance of ±40 mm when the curve has a radius R of about 350 mm. The motion sequence of the overall system can thus occur in a relatively simple way without involved mechanisms and ensures a control of the individual motors M1, M2, M3 as well as the transport means 13 for the film cassette.

Figure 3:
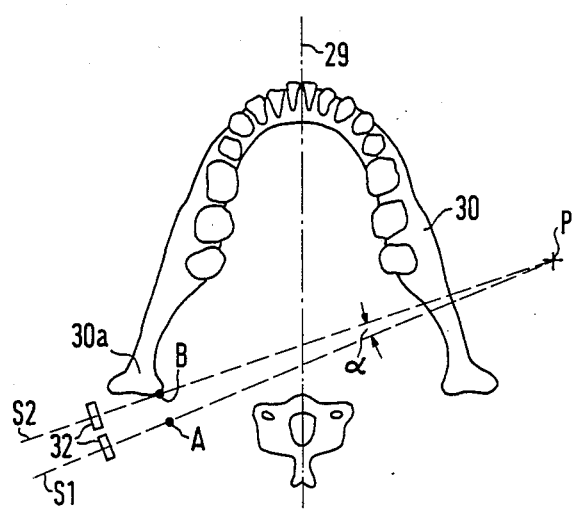
FIG. 3 is a schematic plan view of the jaw of the patient.
Figure 4:
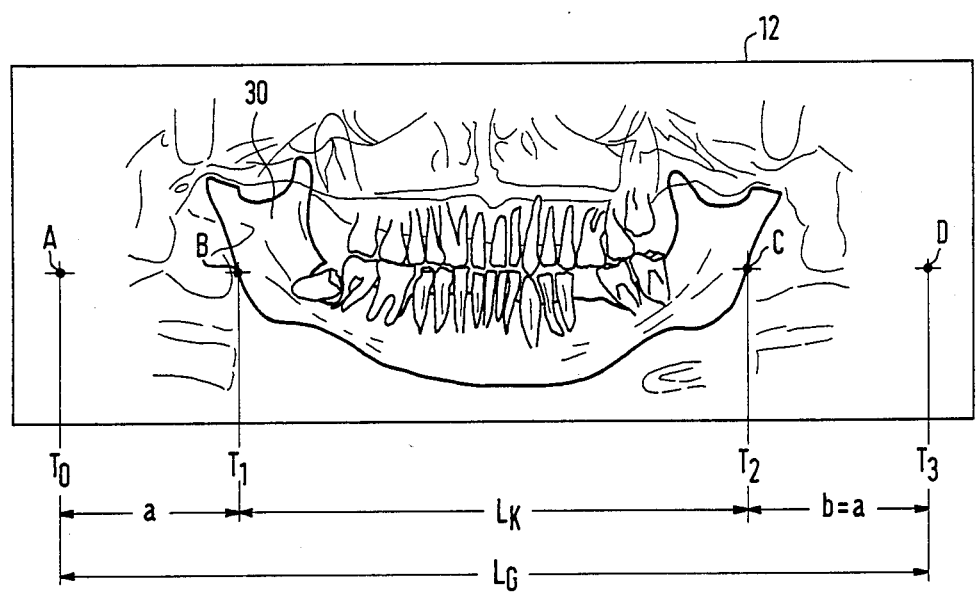
FIG. 4 is a image of the jaw of the patient on film.
Figure 5:
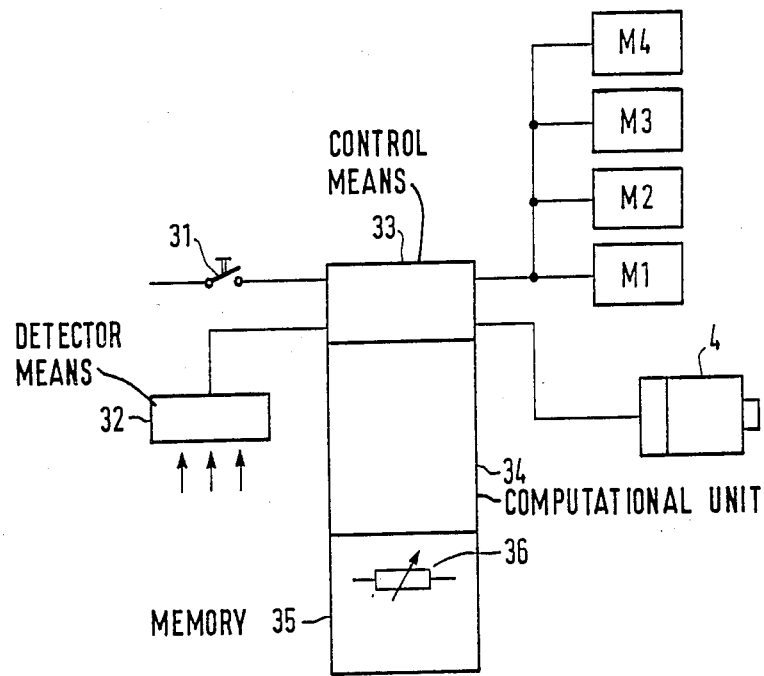
FIG. 5 is a block circuit diagram for the apparatus of the present invention.

The exposure technique in accordance with the invention shall be set forth in greater detail with reference to FIGS. 3 through 5. FIG. 3 schematically shows the jaw of a patient in a plan view, while FIG. 4 shows a simplified view of a panoramic exposure and FIG. 5 provides a schematic circuit diagram or block diagram for the apparatus. The rotary unit 3 of FIG. 1 is first moved into its initial position proceeding from which the radiation source 4 can transilluminate the jaw proceeding from a point P (FIG. 3). This initial position is arbitrarily selectable in and of itself, but should be placed such that the first rays S1 proceeds outside of the one end of the one mandibular arch 30, such as the left mandibular arch 30a as illustrated in the illustration. A detector arrangement or means 32 composed of one or more detectors is arranged in front of or behind the film cassette and receives the radiation dose emitted by the radiation source and form electrical signals dependent on the radiation dosage.

After actuation of the starter key 31 (FIG. 5), the radiation source as well as the drive motors M1–M3 for the rotary unit 3 and the drive motor M4 for the adjustment of the film cassette 12 are switched on at a point-in-time $T_\alpha$ (FIG. 4). The adjustment of the rotary unit thereby occurs with a constant speed.

Assuming that the beginning of the irradiation lies in point A on the film (FIG. 4), then the rays S1 in FIG. 3 lie outside of the left mandibular arch 30a. After the beginning of the transillumination of the patient's head at point A, the incident radiation dose is acquired by means of the detector arrangement 32. This forwards a corresponding signal to a control unit 33 (FIG. 5). In a computation unit 34, which has a comparator circuit, a quantity corresponding to the actual radiation dose is compared to a rated quantity deposited in a memory 35, which rated quantity corresponds to a dose value defined for a specific degree of density for the film, and the appertaining exposure data or settings for mA, kV and time are identified therefrom. The identified quantities are supplied to the control unit 33, which controls the generator for the radiation source 4. In order for the degree of density to be individually determined by the user, the memory 35 contains a variable rated value 36 for the radiation dose.

Since, given some patients, the spinal column can lie in the beam path at the beginning of the irradiation at the starting point P, the dose value measured by the detector arrangement 32 is not suitable for the calculation of the rated dose in such a case. In order to avoid falsification in this regard, it is proposed in accordance with a further, advantageous development of the invention to provide means, which leads to at least one repeated measurement being carried out at a later point in time at which the spinal column can definitely no longer lie in the beam path. This second measurement is employed for the calculation of the rated dose. This means that first there must be a threshold below which the dose measured by the detector arrangement 32 is ignored and secondly at a defined time after which the repetition measurement is carried out.

The detector arrangement or means is advantageously composed of elements which are constructed of a scintillation crystal and of a photodiode. In addition to the identification of the patient-oriented exposure data, the patient associated optimum tomographic layer can also be defined with the arrangement of the invention. To this end, reaching the skip function, i.e., the beginning of the transirradiation of the left mandibular arch is identified by the detector arrangement 32 at point B at time $T_1$ see rays S2 in FIG. 3) after a path distance a on the film (FIG. 4). The detector arrangement 32 registers a dose attenuation at this point. The detector arrangement 32 now forwards an additional signal to the control unit 33. At the same time, the elapsed time from $T_0$ through $T_1$, which is identified by the control unit is reported to the computation unit 34. The computation unit 34 processes this information in that it identifies the length of the jaw $L_K$ in accordance with its development on the film in accord with the relationship $L_K = L_G - 2a$. As mentioned hereinbefore, the jaw width has a direct relationship to the jaw length $L_K$. The unit 34 uses the known running time T ($T_0$ through $T_3$) which is necessary in order to expose the entire jaw and from the likewise known path length $L_G$ from the film from the beginning of the transillumination at point A up to the shut-off of the radiator after the conclusion of the exposure at the point in time $T_3$ and at point D.

Forming the basis thereof is that the exposure occurs systematically relative to the mandibular arch 30 and, thus, to the symmetry axis 29 of the jaw.

The optimum tomographic layer position to be identified for the particular patient can be identified by comparison to film transport speeds that are emperically identified and are allocated to values which are stored in memory 35 for a specific jaw width. From the patient-associated jaw configuration jaw length and jaw width, the computation unit 34 thus identifies the particular film transport speed with which the film drive M4 is controlled via the control unit 33.

Although various minor modifications may be suggested by those adverse in the art, it should be understood that we wish to embody within the scope of the patent granted hereon all such modifications as reasonably and properly come within the scope of our contribution to the art.

We claim:

1. In a dental x-ray diagnostic apparatus for producing panorama tomograms of a jaw of a patient, said apparatus comprising a rotary unit which contains a carrier with a radiation source for producing x-rays and a film cassette holder being mounted on the carrier, said film cassette holder accepting a film cassette containing film, said rotary unit having adjustment means for adjustably rotating the carrier around a first vertical axis with said axis being moved to form an orbit curve for the cassette corresponding to a dental arch, said film cassette holder and cassette being adjustable so that the teeth are successively imaged on the film together with the jaw and contain at least one detector means adjacent the film cassette for creating an electrical signal corresponding to a dose rate of x-rays incident thereon and supplying said electrical signal for the control of at least a tube voltage of the radiation source, the improvements comprising control means for operating the adjustment means to position the rotary unit in an initial position wherein the path of the x-rays from the radiation source proceed outside of one end of a mandibular arch and onto the film cassette, said detector means measuring an incoming x-ray dosage as the rotary unit moves the path from the initial position spaced from the one end to a second position with the path of the x-rays beginning to pass through the one end of the mandibular arch to generate a signal corresponding to the x-ray dosage to supply to a computation unit associated with the control means, said computation unit having means for comparing the quantity corresponding to the signal to a quantity selecting exposure data for mA, kV and time required for transillumination of an appertaining patient's head from said comparison to control the generator of the radiation source so that for an exposure of the jaw the exposure data is selected before the one end of the jaw is reached by the path of the x-ray and remains constant for the entire time for the path of the x-ray to travel the length of the jaw.

2. In an x-ray diagnostic apparatus according to claim 1, wherein the control means includes a memory connected to the computation unit, said memory containing a memory element which supplies a comparison quantity corresponding to the predescribed dose value.

3. In an x-ray diagnostic apparatus according to claim 2, wherein the memory includes memory elements adjustable in terms of its comparison quantity.

4. In an x-ray diagnostic apparatus according to claim 1, wherein the comparison unit has means for identifying patient-associated qualities for jaw length and jaw width for the dosage measurement obtained by the detector means and the patient-associated tomogram position is determined from a comparison of these quantities to prescribed value pairs for film transport speeds allocated to specific jaw dimensions.

5. In an x-ray diagnostic installation according to claim 4, wherein the control means has means for acquiring the time from the beginning of the transillumination of the patient's head up to the beginning of the transillumination of the one end, said computation unit determining the half length of the film up to the beginning of the transillumination of the one end from identifiable time in relationship to the overall running time and from the path distance transverse of the film in this time, the length of the jaw imaged on the film being calculated subsequent thereto and the quantity for the jaw length is calculated therefrom.

6. In an x-ray diagnostic installation according to claim 5 wherein the computation unit is connected to a memory in which a plurality of comparative values for film transport speeds allocated to different jaw widths are deposited, said computation unit identifying the patient-associated jaw width and comparing it to a deposited memory value and the tomogram position corresponding to the personal jaw configuration of the patient being identified from this comparison.

7. In an x-ray diagnostic apparatus according to claim 1 wherein the adjustment means contains first means with which the carrier can be rotated around a first vertical axis, second means which pivot the carrier around a swivel axis with a swivel motion at right angles relative to the symmetry axis of the subject during the rotational movement around the first axis, the distance between the swivel axis and first axis and the excursion of the swivel motion being selected so that a perpendicular transillumination direction through the subject is provided given the motion of the rotary unit giving a constance basing of the subject between the subject and the film and in that further said film cassette is adjustably held in the film holder relative to said radiation source and that said first and second means are controlled by said control means.

8. In an x-ray diagnostic apparatus according to claim 7, wherein the carrier is fashioned as a closed turntable ring which is rotatably mounted in a bearing part connected to a truck, said film cassette being in a film cassette holder arranged on said ring and being adjustably held relative to the radiation source which is mounted on said ring and that said second swivel axis forms a pivot connection between the bearing part and an arm connected to said truck.

9. In an x-ray diagnostic apparatus according to claim 8, wherein the second means includes two pairs of scissor arms having pivotal connections to the truck and to the bearing part on each side of the swivel axis at a prescribed distance, said second means having at least one drive motor being arranged between the point of the pivotal connections of at least one pair of scissor arms.

10. In an x-ray diagnostic apparatus according to claim 9, wherein a spindle drive is provided between the point of pivotal connections of each pair of scissor arms, said arm extending between the truck and the bearing part being a telescopic arm allowing movement of the ring by said pair of spindle drives to and from said truck.

11. In an x-ray diagnostic apparatus according to claim 1, wherein the means for comparing the dose value represents a rated value and includes means for determining a threshold below which the dose measured by said detector arrangement remains unconsidered and includes second means which defines a time after whose expiration a repeated measurement is carried out.

12. In an x-ray diagnostic apparatus according to claim 1, wherein the detector means is an electro-optic detector arrangement including elements which are constructed of a scintillation crystal and a photodiode.

* * * * *